(12) United States Patent
Hirose et al.

(10) Patent No.: US 10,314,916 B2
(45) Date of Patent: Jun. 11, 2019

(54) CARRIER FOR DELIVERY OF SUBSTANCE TO PHAGOCYTES

(71) Applicant: HOUSE WELLNESS FOODS CORPORATION, Hyogo (JP)

(72) Inventors: Yoshitaka Hirose, Hyogo (JP); Shinji Murosaki, Nara (JP); Yoshihiro Yamamoto, Hyogo (JP)

(73) Assignee: House Wellness Foods Corporation, Itami (JP)

( * ) Notice: Subject to any disclaimer, the term of this patent is extended or adjusted under 35 U.S.C. 154(b) by 0 days.

(21) Appl. No.: 14/897,722

(22) PCT Filed: Jun. 11, 2013

(86) PCT No.: PCT/JP2013/066108
§ 371 (c)(1),
(2) Date: Dec. 11, 2015

(87) PCT Pub. No.: WO2014/199448
PCT Pub. Date: Dec. 18, 2014

(65) Prior Publication Data
US 2016/0144041 A1 May 26, 2016

(51) Int. Cl.
*A61K 47/46* (2006.01)
*C12N 1/20* (2006.01)
*A61K 47/69* (2017.01)

(52) U.S. Cl.
CPC .......... *A61K 47/46* (2013.01); *A61K 47/6901* (2017.08); *C12N 1/20* (2013.01)

(58) Field of Classification Search
None
See application file for complete search history.

(56) References Cited

U.S. PATENT DOCUMENTS

| | | | |
|---|---|---|---|
| 2001/0006642 A1 | 7/2001 | Steidler et al. | |
| 2003/0202991 A1* | 10/2003 | Steidler | C07K 14/33 424/243.1 |
| 2004/0208863 A1 | 10/2004 | Versalovic et al. | |
| 2008/0254011 A1* | 10/2008 | Rothschild | A61K 35/747 424/93.45 |
| 2009/0136454 A1* | 5/2009 | Versalovic | A61K 35/744 424/93.4 |
| 2010/0098728 A1* | 4/2010 | Fujiki | A23C 20/025 424/246.1 |
| 2011/0081328 A1 | 4/2011 | Rothschild et al. | |
| 2011/0217368 A1 | 9/2011 | Prakash et al. | |
| 2013/0052171 A1* | 2/2013 | Chang | C12R 1/225 424/93.45 |

FOREIGN PATENT DOCUMENTS

| | | |
|---|---|---|
| EP | 1084709 A1 | 3/2001 |
| JP | 2000-508162 A | 7/2000 |
| JP | 2001-064174 A | 3/2001 |
| JP | 2002-080364 * | 3/2002 |
| JP | 2005-068092 A | 3/2005 |
| JP | 2006-519014 A | 8/2006 |
| JP | 2009057344 A | 3/2009 |
| JP | 2010-095465 A | 4/2010 |
| JP | 2010-523144 A | 7/2010 |
| WO | 2005/079854 A1 | 9/2005 |
| WO | 2011/150127 A2 | 12/2011 |

OTHER PUBLICATIONS

Martinez et al., Pharmacol. Rev., vol. 63, pp. 967-1000, 2011.*
Hey et al., J. Cell. Mol. Med. vol. 16, No. 11, 2012 pp. 2611-2619.*
Murozaki JP2002-080364 machine translation, Mar. 2002.*
Osganian et al., Journal of the American College of Cardiology, vol. 42, No. 2, 2003.*
Translation of Murooka et al., 2003, Japanese Journal of Lactic Acid Bacteria vol. 14 (2), p. 72-79.*
Hiroshi Suzuki et al., Nature vol. 386 (6622), p. 292-296 (Mar. 20, 1997).
Thomas Areschoug et al., Cellular Microbiology vol. 11 (8), p. 1160-1169 (Aug. 2009).
Zvjezdana Sever-Chroneos et al., The Journal of Biological Chemistry vol. 286 (6), p. 4854-4870 (Feb. 11, 2011).
Yukio Fujiwara et al., Arterioscler Thromb Vasc Biol. vol. 27 (11), p. 2400-2406 (Nov. 2011).
Ajay Chawla et al., Nature Medicine vol. 7 (1), p. 48-52 (Jan. 2001).
Nanlan Luo et al., Atherosclerosis. vol. 228 (1), p. 124-135 (May 2013).
Yoshikatsu Murooka et al., Japanese Journal of Lactic Acid Bacteria vol. 14 (2), p. 72-79.
Toshifumi Hibi et al., Drug Delivery System, vol. 19(2); p. 84-89, Abstract only.
Takahiro Okuno et al., Abstracts of Annual Meeting of Pharmaceutical Society of Japan vol. 129(3); p. 172.
English Abstract of JP-2009-057344A, cited as a reference in corresponding Japanese Patent Application No. 2015-522296, 1 page.
Machine Translation of JP-2009-057344A, cited in corresponding Japanese Patent Application No. 2015-522296, 17 pages.
International Search Report issued in corresponding International Application Ser. No. PCT/JP2013/066108, filed Jun. 11, 2013, 4 pages.
Detmer, Ann, et al., "Live bacterial vaccines—a review and identification of potential hazards", Jun. 23, 2006, 12 pages.
Extended European Search Report dated Jan. 18, 2017 in corresponding European Patent Application No. 13886888.0, 9 pages.
Marie-Claude Geoffroy et al. Use of Green Fluorescent Protein to Tag Lactic Acid Bacterium Strains under Development as Live Vaccine Vectors. Applied and Environmental Microbiology, Jan. 2000, vol. 66, No. 1, pp. 383-391.

(Continued)

*Primary Examiner* — David W Berke-Schlessel
(74) *Attorney, Agent, or Firm* — Mintz Levin Cohn Ferris Glovsky and Popeo, P.C.

(57) ABSTRACT

An object of the present invention is to provide a low-cost and safe approach to efficient delivery of a substance to phagocytes. In particular, the present invention relates to a carrier for delivery of a substance to phagocytes, the carrier comprising a lactic acid bacterium and/or an extract thereof.

7 Claims, No Drawings

(56) References Cited

OTHER PUBLICATIONS

Murosaki, Shinji et al., Heat-killed Lactobacillus Plantarum L-137 Suppresses Naturally Fed Antigen-Specific IgE Production by Stimulation of IL-12 Production in mice, Basic and Clinical Ummunology, vol. 102, No. 1, Jul. 1998, pp. 57-64.

Hirose, Yoshitaka et al., Oral intake of heat-killed Lactobacillus plantarum L-137 decreases the incidence of upper respiratory tract infection in healthy subjects with high levels of psychological stress, Nutritional Immunology, Journal of Nutritional Science, 2013, vol. 2, pp. 1-8.

Hirose, Yoshitaka et al., Lipoteichoic acids on Lactobacillus plantarum cell surfaces correlate with induction of interleukin-12p40 production, Microbial Immunollogy 2010, 54: 143-151.

Hirose, Yoshitaka et al., Daily intake of heat-killed Lactobacillus plantarum L-137 Augments Acquired Immunity in healthy adults, Nutritional Immunology, 2006, 3069-3073.

* cited by examiner

CARRIER FOR DELIVERY OF SUBSTANCE TO PHAGOCYTES

RELATED APPLICATIONS

This application is the U.S. national stage pursuant to 35 U.S.C. § 371, of Japanese international application Ser. No. PCT/JP2013/066108, filed Jun. 11, 2013 and published in Japanese on Dec. 18, 2014 as publication WO2014/199448 A1, which is hereby expressly incorporated by reference in its entirety.

TECHNICAL FIELD

The present invention relates to a drug delivery carrier for delivery of a substance to phagocytes, the carrier comprising a lactic acid bacterium.

BACKGROUND ART

Phagocytes in the body play a pivotal role in innate immunity, particularly in removal of foreign substances and waste products by their phagocytosis. Phagocytes are considered to also play an important role in the modulation of acquired immunity by their antigen processing function. In contrast to these roles, it is known that acceleration of phagocyte activity or function in the body may lead to pathological conditions.

Diseases caused by acceleration of phagocyte activity or function are, for example, atherosclerosis, congestive heart failure, ischemic diseases, restenosis, hypertension, fibrotic vasculopathies (diabetes, systemic lupus erythematosus, etc.), neurodegenerative diseases (e.g., Alzheimer's disease, Huntington's disease, Parkinson's disease, spinocerebellar degeneration, amyotrophic lateral sclerosis, etc.), brain injury, cerebrovascular events (e.g., strokes, seizures, nerve injury, regeneration in the central nervous system, etc.), hematopoietic disorders, adult respiratory distress syndrome (ARDS), cancers (leukemias, particularly adult T-cell leukemia), solid cancers, autoimmune diseases, infections (e.g., HIV infection, AIDS, etc.), fibroproliferative disorders (e.g., psoriasis), chronic and acute inflammatory diseases (e.g., rheumatoid arthritis, Crohn's disease, inflammatory bowel syndrome, etc.), glomerulopathies, sepsis, graft rejection, graft versus host disease, osteopathies, cardiac and non-cardiac vascular disease states that can be characterized by aberrant fibroproliferative/inflammatory responses, for example, diseases characterized by infiltration of leukocytes at an injury site, such as oxygen- or glucose-deficient tissue resulting from the diseases (e.g., cerebral apoplexy, myocardial infarction, etc.), among others.

Phagocytes present in various tissues in the body mostly express scavenger receptors, which contribute to phagocytosis of foreign substances. Scavenger receptors are known to have an affinity to various types of particles with a negative charge and to mediate phagocytosis of LDL modified by oxidation, acetylation, glycosylation, etc. as well as of foreign bacteria in the body and their components (Non Patent Literature 1 to 3). The expression of scavenger receptors is not regulated by the amount of modified LDL taken up by phagocytes, and consequently phagocytes take up modified LDL indefinitely. Phagocytes overladen with modified LDL form foam cells in the tunica intima and then induce atherosclerosis.

Based on the above fact that atherosclerosis is induced by phagocytes overladen with modified LDL, it is considered that atherosclerosis may be effectively prevented and treated by efficient phagocyte-targeted delivery of, for example, a compound having inhibitory effect on foam cell formation (e.g., esculeogenin A (Non Patent Literature 4), a PPARγ agonist (Non Patent Literature 5), adiponectin (Non Patent Literature 6), etc.), an enzyme that metabolizes or decomposes modified LDL accumulated in phagocytes (Non Patent Literature 7), or the like. Various studies are conducted for this purpose today.

One example of conventional approaches to efficient delivery of a drug to phagocytes is use of a targeting liposome. However, the production of a targeting liposome requires a complicated chemical synthesis and purification process, and thus there are many problems in an attempt to make such a targeting liposome industrially applicable.

For these reasons, there have been demands for the development of a highly safe carrier that delivers a substance to phagocytes at a high efficiency and is easily produced at relatively low cost.

CITATION LIST

Non Patent Literature

Non Patent Literature 1: Nature. 1997 Mar. 20; 386(6622): 292-6.
Non Patent Literature 2: Cell Microbiol. 2009 August; 11(8):1160-9.
Non Patent Literature 3: J Biol Chem. 2011 Feb. 11; 286(6):4854-70.
Non Patent Literature 4: Arterioscler Thromb Vasc Biol. 2007 November; 27(11):2400-6.
Non Patent Literature 5: Nat Med. 2001; 7(1):48-52.
Non Patent Literature 6: Atherosclerosis. 2013; 228(1):124-35.
Non Patent Literature 7: Japanese Journal of Lactic Acid Bacteria. Vol. 14 (2003) No. 2, 72-79.

SUMMARY OF INVENTION

Technical Problem

An object of the present invention is to provide a low-cost and safe carrier for efficient delivery of a substance (for example, a drug, a medicament, etc.) to phagocytes and an approach to efficient delivery of a substance to phagocytes.

Solution to Problem

The inventors conducted extensive study to solve the above problems and, as a result, surprisingly found that lactic acid bacteria are efficiently taken up by phagocytes. The inventors carried out further research and found that lactic acid bacteria have a high affinity to the scavenger receptor of phagocytes, which leads to a high uptake of lactic acid bacteria by phagocytes. The inventors further performed a variety of examinations and completed the present invention.

That is, the present invention relates to the following.
(1) A carrier for delivery of a substance to phagocytes, the carrier comprising a lactic acid bacterium and/or an extract thereof.
(2) The carrier according to the above (1), wherein the lactic acid bacterium belongs to the genus *Lactobacillus*.
(3) The carrier according to the above (1), wherein the lactic acid bacterium is a *Lactobacillus plantarum* strain.
(4) The carrier according to the above (1), wherein the lactic acid bacteria is *Lactobacillus plantarum* L-137 strain.

(5) The drug carrier according to any one of the above (1) to (4), wherein the lactic acid bacterium is dead.
(6) The carrier according to any one of the above (1) to (5), wherein the delivery of a substance to phagocytes is mediated by a scavenger receptor of the phagocytes.
(7) The carrier according to the above (6), wherein the scavenger receptor is a class A scavenger receptor.
(8) The carrier according to any one of the above (1) to (7), wherein the substance is a substance used to diagnose, prevent and/or treat a phagocyte-related disease.
(9) The carrier according to the above (8), wherein the phagocyte-related disease is atherosclerosis.
(10) A composition comprising the carrier according to any one of the above (1) to (9) and a substance to be delivered to phagocytes.
(11) A method for delivering a substance to phagocytes by using the carrier according to any one of the above (1) to (9).

Advantageous Effects of Invention

The present invention provides a carrier for efficient delivery of various types of desired substances to phagocytes. The present invention also provides a carrier that can be effectively used for diagnosis, prevention or treatment of a phagocyte-related disease (e.g., atherosclerosis etc.) in cases where the substance to be delivered is, for example, a drug for the phagocyte-related disease, and a composition comprising the carrier.

The present invention uses lactic acid bacteria, which are safe, can be mass cultured and mass produced, are relatively easy to genetically engineer, and have other advantages. Therefore, according to the present invention, a highly safe carrier that effectively delivers a substance to phagocytes can be produced at low cost.

DESCRIPTION OF EMBODIMENTS

The present invention will be described in detail below.
The present invention relates to a carrier for delivery of a substance to phagocytes. The carrier of the present invention comprises lactic acid bacterial cells or an extract thereof. In preferred embodiments of the present invention, the lactic acid bacterial cells or an extract thereof contained in the carrier allows highly efficient delivery of a substance to phagocytes.

The lactic acid bacterium used in the carrier of the present invention is not particularly limited and may be a known lactic acid bacterium, for example, those belonging to the genus *Lactobacillus*, the genus *Streptococcus*, the genus *Enterococcus*, the genus *Lactococcus* and the genus *Bifidobacterium*. Specific examples thereof include *Lactobacillus plantarum, Lactobacillus acidophilus, Lactobacillus brevis, Lactobacillus casei, Lactobacillus fermentum, Lactobacillus paracasei, Lactobacillus buchneri, Lactobacillus delbrueckii, Lactobacillus rhamnosus, Streptococcus thermophilus, Enterococcus faecalis, Enterococcus faecium, Lactococcus lactis, Lactococcus plantarum, Bifidobacterium thermophilum, Bifidobacterium longum, Bifidobacterium breve*, etc. Of these types of lactic acid bacteria, the lactic acid bacteria belonging to the genus *Lactobacillus* are preferred due to their excellent performance of delivering a molecule. Particularly preferred is a *Lactobacillus plantarum* strain.

Representative examples of preferred *Lactobacillus plantarum* strains used in the present invention include *Lactobacillus plantarum* L-137 strain (deposited in National Institute of Bioscience and Human-Technology, Agency of Industrial Science and Technology under Accession No. FERM P-15317 on Nov. 30, 1995), *Lactobacillus plantarum* JCM 1149 reference strain, and *Lactobacillus plantarum* L-051 strain (FERM P-11912). Particularly preferred are *Lactobacillus plantarum* L-137 strain etc.

The lactic acid bacterium used in the present invention may be those cultured in a culture medium such as a natural medium, a synthetic medium and a semi-synthetic medium. In the present invention, culture of the lactic acid bacterium may be performed in accordance with a known method, a conventional method or an equivalent method thereof.

The culture medium is not particularly limited, but preferred are, for example, those containing a nitrogen source and/or a carbon source. The nitrogen source is not particularly limited, and examples thereof include, meat extract, peptone, gluten, casein, yeast extract, amino acids, etc. The carbon source is not particularly limited, and examples thereof include glucose, xylose, fructose, inositol, maltose, starch syrup, koji extract, starch, bagasse, wheat bran, molasses, glycerol, etc. These may be used alone or in combination of two or more of them.

The culture medium may further contain a mineral in addition to the nitrogen source and/or the carbon source. The mineral is not particularly limited, and examples thereof include ammonium sulfate, potassium phosphate, magnesium chloride, sodium chloride, iron, manganese, molybdenum, various types of vitamins, etc. These may be used alone or in combination of two or more of them.

The culture temperature and the culture time of the lactic acid bacterium are not particularly limited as long as the bacterium can be efficiently cultured. In one embodiment of the present invention, the culture temperature may be, for example, usually about 25 to 40° C., preferably about 27 to 35° C., and the culture time may be, for example, about 12 to 48 hours. In one embodiment of the present invention, the lactic acid bacterium may be cultured with aeration and shaking. The pH of the culture medium is not particularly limited, and in one embodiment of the present invention, the pH may be usually about 3 to 6, preferably about 4 to 6.

The lactic acid bacterial cells used in the present invention may be living or dead, but preferred are dead cells because they are stable, easy to handle and have other advantages. The process for preparing the dead cells of the lactic acid bacterium will be specifically described below.

In the present invention, the preparation process for the dead cells of the bacterium is not particularly limited as long as the effects of the present invention are not lost. The dead cells of the bacterium may be prepared by, for example, (I) separating living cells of the lactic acid bacterium from a liquid medium at the end of culture, and performing sterilization to kill the living cells and give dead cells, or (II) sterilizing a liquid medium containing living cells of the lactic acid bacterium to kill the living cells, and separating the dead cells from the liquid medium.

The separation method of the bacterial cells from a liquid medium may be any method usually employed in this field, and is not particularly limited. Specifically, in one embodiment of the present invention, the bacterial cells may be separated from a liquid medium by, for example, adding distilled water to the liquid medium, and removing the supernatant by centrifugation etc. In this embodiment, after the addition of distilled water to the liquid medium and the subsequent centrifugation and the removal of the supernatant, the procedure of adding distilled water to the residue obtained by the removal of the supernatant and subjecting the suspension to centrifugation may be repeated several times, if desired. In one embodiment of the present invention, the separation process may include a filtration step.

The sterilization to kill the living cells of the lactic acid bacterium will be specifically described below. The sterilization method is not particularly limited, and the sterilization may be performed by, for example, heating, UV irradiation, formalin treatment, etc. The sterilization may be performed on harvested living cells or on a liquid medium comprising living cells.

When the sterilization is done by heating, the heating temperature is not particularly limited and may be, for example, usually about 60 to 100° C., preferably about 70 to 90° C. The heating means is not particularly limited, and may be in accordance with a known method, for example, a method using a heater etc. The heating time is not particularly limited as long as sterilization is sufficiently completed, and heating may be carried out, for example, usually for about 5 to 40 minutes, preferably for about 10 to 30 minutes, after the temperature reaches a desired level.

The dead cells prepared as above may be subjected to grinding, disruption or lyophilization to give processed dead cells. In the present invention, such processed dead cells are also suitable as dead cells.

In the present invention, an extract of the lactic acid bacterial cells may be used instead of or together with the bacterial cells. The extraction method for obtaining the extract is not particularly limited, and the extraction may be performed by a known method, a conventional method or an equivalent method thereof. Specifically, the extraction may be performed by, for example, (i) adding the living or dead cells of the lactic acid bacterium to an extraction solvent at room or elevated temperature under normal or reduced pressure, and performing extraction by immersion or stirring, or (ii) adding the living or dead cells of the lactic acid bacterium to an extraction solvent, and performing extraction by reflexing. The extraction temperature and the extraction time may be selected as appropriate depending on the type of extraction solvent used and the extraction conditions.

The extraction solvent is not particularly limited and may be, for example, water, an organic solvent, or a mixed solvent thereof at any mixing ratio. The organic solvent is not particularly limited and examples thereof include alcohols that are liquid at room temperature, such as lower alcohols (e.g., methanol, ethanol, n-propanol, isopropanol, n-butanol, etc.) and polyalcohols (e.g., 1,3-butylene glycol, propylene glycol, glycerol, etc.); ethers (e.g., diethyl ether, propyl ether, etc.); esters (e.g., ethyl acetate, butyl acetate, etc.); ketones (e.g., acetone, ethyl methyl ketone, etc.); hydrocarbons (e.g., hexane, xylene, toluene, etc.); chloroform; etc. These may be used alone or in combination of two or more of them. Of these organic solvents, preferred are alcohols that are liquid at room temperature, for example, lower alcohols of 1 to 4 carbon atoms, in terms of operability, environmental concerns, etc. More preferred is ethanol in terms of safety concerns over residual solvent.

In the present invention, the mixture containing the extract and the residue obtained by the above extraction process may be, if desired, filtered or centrifuged to remove the residual solid material. The resulting extract may be directly used for the preparation of the carrier of the present invention, or alternatively dried and/or powdered by concentration, lyophilization, spray-drying, or other methods and then used for the preparation of the carrier of the present invention.

The carrier of the present invention comprises the bacterial cells or the extract and is thus taken up by phagocytes at a high efficiency. Hence, the carrier of the present invention is highly suitable as a carrier for efficient delivery of a desired substance to phagocytes.

In the present invention, the phagocytes are not particularly limited, and preferably include macrophages, monocytes, polymorphonuclear leukocytes, dendritic cells, etc.

The substance to be delivered by the carrier of the present invention to phagocytes is not particularly limited, and examples thereof include a functional substance. The functional substance is preferably a substance that has the function of exhibiting an effect of some kind after delivered to phagocytes, and examples thereof include atoms, molecules, compounds, peptides, proteins, nucleic acids, vectors, viruses, cells, etc. The "effect of some kind" is not particularly limited, and may be a desirable or useful effect or a harmful action. The "harmful action" can be used in study and research, or, in cases where phagocytes that exhibit an undesirable effect on the body exist, can be used to inhibit or eliminate the effect of the phagocytes. That is, the type of the functional substance may be selected depending on the purpose of use of the carrier of the present invention.

In one embodiment of the present invention, the functional substance may be, for example, a compound having inhibitory effect on foam cell formation of macrophages (e.g., esculeogenin A, a PPARγ agonist, adiponectin, etc.); an enzyme that metabolizes or decomposes cholesterol accumulated in macrophages through their uptake of oxidized LDL (e.g., cholesterol oxidase (ChoA) etc.); an inflammatory cytokine that contributes to the activation of phagocytes (e.g., IL-1β etc.); a fluorochrome useful for detection and identification of cells (e.g., fluorescein isothiocyanate (FITC) etc.); or the like.

In a preferred embodiment of the present invention, the functional substance is a substance used to diagnose, prevent and/or treat a phagocyte-related disease.

The phagocyte-related disease is not particularly limited, and examples thereof include atherosclerosis, congestive heart failure, ischemic diseases, restenosis, hypertension, fibrotic vasculopathies (diabetes, systemic lupus erythematosus, etc.), neurodegenerative diseases (e.g., Alzheimer's disease, Huntington's disease, Parkinson's disease, spinocerebellar degeneration, amyotrophic lateral sclerosis, etc.), brain injury, cerebrovascular events (e.g., strokes, seizures, nerve injury, regeneration in the central nervous system, etc.), hematopoietic disorders, adult respiratory distress syndrome (ARDS), cancers (leukemias, particularly adult T-cell leukemia), solid cancers, autoimmune diseases, infections (e.g., HIV infection, AIDS, etc.), fibroproliferative disorders (e.g., psoriasis), chronic and acute inflammatory diseases (e.g., rheumatoid arthritis, Crohn's disease, inflammatory bowel syndrome, etc.), glomerulopathies, sepsis, graft rejection, graft versus host disease, osteopathies, cardiac and non-cardiac vascular disease states that can be characterized by aberrant fibroproliferative/inflammatory responses, for example, diseases characterized by infiltration of leukocytes at an injury site, such as oxygen- or glucose-deficient tissue resulting from the diseases (e.g., cerebral apoplexy, myocardial infarction, etc.), among others.

In one embodiment of the present invention, the substance used to diagnose, prevent and/or treat a phagocyte-related disease may be, for example, esculeogenin A, a PPARγ agonist, adiponectin, ChoA, or the like when the purpose of use is the prevention and/or amelioration of atherosclerosis.

In the present invention, the substance to be delivered to phagocytes may be loaded onto the carrier of the present invention. Alternatively, the substance to be delivered to phagocytes may simply be mixed with the carrier of the present invention.

The method for loading the carrier of the present invention with a substance to be delivered to phagocytes will be described below.

The loading method is not particularly limited as long as the effects of the present invention are not lost and, for example, a substance to be delivered to phagocytes may be bound to the surface and/or inside of the lactic acid bacterial cells or bound to the lactic acid bacterial extract. The types of bonding is not particularly limited and may be, for example, chemical bonding including covalent bonding, polar covalent bonding, ionic bonding, electrostatic bonding, coordinate covalent bonding, aromatic binding, hydrogen bonding, dipole-dipole interaction, and van der Waals interaction. Alternatively, a substance to be delivered to phagocytes may be loaded onto the bacterial cells through gene engineering, by allowing the substance to be expressed and produced on the surface of the bacterial cells and/or in the inside of the bacterial cells.

The loading method will be more specifically described below.

In one embodiment of the present invention where a fluorescent-labeling agent (e.g., FITC isomer-I (Dojindo Laboratories)) is loaded onto the surface of the lactic acid bacterium, the loading can be achieved by reacting the fluorescent-labeling agent with the bacterium under protection from light. The reaction conditions may include, for example, a temperature of about 30 to 45° C. and a reaction time of about 10 to 120 minutes.

In another embodiment of the present invention where cholesterol oxidase (ChoA) is loaded onto the lactic acid bacterium, the loading may be achieved by fusing a plasmid derived from the lactic acid bacterium to an *Escherichia coli*-derived plasmid carrying the choA gene under any given conditions to construct, for example, plasmid pWK7 (see, J Biosci Bioeng. 2001; 92(5): 459-65.), and introducing, for example, via electroporation, the constructed plasmid into the lactic acid bacterium to allow the transformation of the bacterium.

The application of gene engineering technique will allow loading of the lactic acid bacterium with, for example, adiponectin (see, e.g., Atherosclerosis. 2013; 228(1): 124-35.), IL-1β (see, e.g., Clin Vaccine Immunol. 2010; 17(1): 43-8.), or the like.

The carrier of the present invention may further comprise, in addition to the lactic acid bacterial cells and/or the extract, a component other than lactic acid bacteria. The component is not particularly limited as long as the effects of the present invention are not lost, and may be any component known in the field of medicines, pharmaceuticals, food, etc. In one embodiment of the present invention, the component other than lactic acid bacteria is preferably one having a high affinity to the lactic acid bacterial cells and/or the extract, one that can bind to the lactic acid bacterial cells and/or the extract, or the like. Examples of such a component include lipids, sterols, vegetable oils, mineral oils and lecithins.

The carrier of the present invention may further comprise a substance that promotes the uptake by phagocytes, such as a targeting agent. The term. "targeting agent" preferably refers to a compound that shows selectivity for a specific target organ or tissue. The targeting agent may be any type of compound usually used in this field and is not particularly limited. Examples thereof include a retinoid etc.

The amount of the lactic acid bacterial cells and/or extract in the carrier of the present invention is not particularly limited as long as the effects of the present invention are exhibited, and may be, for example, about 1 to 100% by mass in 100% by mass of the drug carrier. The amount of the substance loaded onto or mixed with the carrier of the present invention for the purpose of delivery to phagocytes is not particularly limited as long as the effects of the present invention are not impaired, and may be, for example, about 10 to 300 parts by mass based on 100 parts by mass of the carrier of the present invention.

Another embodiment of the present invention relates to a composition comprising the carrier of the present invention and a substance to be delivered to phagocytes. The substance to be delivered to phagocytes is preferably the above-described functional substance. The composition in this embodiment may be, for example, but is not limited to, a pharmaceutical product, a food or drink product, a feed, a food additive, a feed additive, or the like, and is preferably a pharmaceutical product or the like.

Use of the carrier of the present invention for production of a medicament is also included in the present invention.

The pharmaceutical product of the present invention will be described below.

The route of administration of the pharmaceutical product is not particularly limited, and the pharmaceutical product may be administered to a mammal by an oral or parenteral route.

The dosage form of the pharmaceutical product is not particularly limited and may be selected depending on the route of administration. The dosage form may be, for example, an oral or parenteral preparation.

Examples of the oral preparation include granules, powders, tablets (including sugar-coated tablets), pills, capsules, syrups, emulsions, suspensions, etc. The parenteral preparation is not particularly limited and examples thereof include injections (e.g., subcutaneous, intravenous, intramuscular, and intraperitoneal injections, etc.), intravenous infusion, external preparations (e.g., transnasal preparations, transdermal preparations, ointments, etc.), suppositories (e.g., rectal suppositories, vaginal suppositories, etc.), etc.

The pharmaceutical product of the present invention may be produced by a method usually used in this field. The pharmaceutical product may further comprise, for example, a pharmaceutically acceptable carrier, in addition to the carrier of the present invention and the functional substance. Examples of the pharmaceutically acceptable carrier includes excipients, binders, diluents, additives, fragrances, buffering agents, thickeners, colorants, stabilizers, emulsifiers, dispersants, suspending agents, preservatives, etc. More specific examples of the pharmaceutically acceptable carrier include magnesium carbonate, magnesium stearate, talc, sugar, lactose, pectin, dextrin, starch, gelatin, tragacanth, methylcellulose, sodium carboxymethyl cellulose, low melting wax, cacao butter, etc. These may be used alone or in combination of two or more of them.

The oral preparation may be a solid preparation (e.g., tablets, pills, capsules, powders, granules, etc.). The solid preparation may be prepared by mixing the active ingredient with an excipient, a binder, a disintegrant, a lubricant, a stabilizer, a solubilizing agent, or the like in accordance with a conventional method. Examples of the excipient include lactose, mannitol, glucose, microcrystalline cellulose, starch, etc. Examples of the binder include hydroxypropyl cellulose, polyvinylpyrrolidone, magnesium aluminometasilicate, etc. Examples of the disintegrant include calcium cellulose glycolate etc. Examples of the lubricant include magnesium stearate etc. Examples of the solubilizing agent include glutamic acid, aspartic acid, etc. If desired, the preparation may be coated with a coating agent (e.g., saccharose, gelatin, hydroxypropyl cellulose, hydroxypropyl methylcellulose phthalate, etc.) and the coating may have two layers or more.

The oral preparation may be a liquid preparation (e.g., solutions, suspensions, emulsions, syrups, elixirs, etc.). The liquid preparation may be prepared by dissolving, suspending or emulsifying the active ingredient in a commonly used diluent (e.g., purified water, ethanol, or a mixture of them, etc.). The liquid preparation may further comprise a moistening agent, a suspending agent, an emulsifier, a sweetener, a flavor, a fragrance, a preservative, a buffering agent, etc.

The parenteral preparation in the form of an injection as one embodiment of the pharmaceutical product of the present invention includes, for example, a solution, a suspension, an emulsion, and a solid preparation that is dissolved or suspended in a solvent and reconstituted to form an injectable liquid at the time of use. The injection may be prepared by, for example, dissolving, suspending or emulsifying the active ingredient in a solvent. Examples of the solvent include distilled water for injection, physiological saline, a vegetable oil, an alcohol such as propylene glycol, polyethylene glycol and ethanol, etc., and these may be used alone or in combination of two or more of them. The injection may further comprise a stabilizer, a solubilizing agent (e.g., glutamic acid, aspartic acid, polysorbate 80 (registered trademark), etc.), a suspending agent, an emulsifier, a soothing agent, a buffering agent, a preservative, or the like. The preparation process of the injection may further include sterilization or aseptic treatment in the final step.

Alternatively, an aseptic solid preparation, for example, a lyophilized preparation, may be produced. Such an aseptic solid preparation may be dissolved in sterilized distilled water for injection or other solvents prior to use.

The dosage of the pharmaceutical product of the present invention is not particularly limited, and may be selected as appropriate depending on the purpose. The dosage may be determined depending on the type and severity of the disease; the route of administration; the subject to which the pharmaceutical product is to be administered; the age, sex, condition, etc. of the subject; the type of the functional substance loaded onto or mixed with the carrier of the present invention; and other conditions.

The subject to which the pharmaceutical product of the present invention is to be administered is not particularly limited, and may be any types of animals, for example, mammals (humans, mice, rats, horses, dogs, cats, rabbits, pigs, cattle, etc.), or the like.

The food or drink product of the present invention will be described below.

The food or drink product of the present invention may contain one or more types of food additives commonly used in food or drink products, and examples of the food additives include sweeteners, colorants, preservatives, thickeners, antioxidants, color fixatives, bleaching agents, antifungal agents, gum bases, bittering agents, enzymes, brighteners, acidulants, seasonings, emulsifiers, fortifiers, processing aids, flavors, and spice extracts. The food or drink product of the present invention includes health foods, functional foods, foods for specified health use, foods for babies, foods for small children, foods for pregnant women and nursing mothers and foods for sick people.

The form of the food or drink product of the present invention is not particularly limited. Specific examples thereof include so-called dietary supplements in the form of tablets, granules, powders, energy drinks, etc. Other examples thereof include drinks such as tea drink, refreshing drink, carbonated drink, nutritional drink, fruit juice, and lactic drink; noodles such as buckwheat noodle, wheat noodle, Chinese noodle, and instant noodle; sweets and bakery products such as drop, candy, gum, chocolate, snack, biscuit, jelly, jam, cream, pastry, and bread; fishery and livestock products, such as fish sausage, ham, and sausage; dairy products such as processed milk and fermented milk; fats, oils and processed foods thereof, such as vegetable oil, oil for deep frying, margarine, mayonnaise, shortening, whipped cream, and dressing; seasonings such as sauce and dipping sauce; retort pouch foods such as curry, stew, rice-bowl cuisine, porridge, and rice soup; and frozen desserts, such as ice cream, sherbet, and shaved ice.

The intake of the food or drink product of the present invention is not particularly limited, and may be determined depending on the form of the food or drink product; the age, sex, condition, etc. of the subject who is to take the food or drink product; the type of the functional substance loaded onto or mixed with the carrier of the present invention; and other conditions.

The route of delivery of a substance from the carrier of the present invention to phagocytes will be described below.

The delivery of a substance from the carrier of the present invention to phagocytes is preferably mediated by a scavenger receptor. The scavenger receptor is not particularly limited but is preferably a class A scavenger receptor. Examples of the class A scavenger receptor include scavenger receptors AI and AII (antigen receptor CD204 recognized by monoclonal antibody Clone 2F8), etc.

The present invention also includes a method for delivering a substance to phagocytes by using the carrier of the present invention. The substance to be delivered to phagocytes may be as described above, and the delivery may be mediated by the above scavenger receptor.

EXAMPLES

The present invention will be described in more detail with reference to Examples, but is not limited thereto. Various modifications are possible within the technical idea of the present invention by a person who has ordinary knowledge in the art.

Example 1

*Lactobacillus plantarum* L-137 (Accession No. FERM BP-08607) strain was seeded in MRS (de Man, Rogosa, Sharpe) liquid medium and cultured at 32° C. for 24 hours. After the culture, the liquid medium was centrifuged at 4,200×g at 4° C. for 10 minutes and the bacterial cells were recovered. The bacterial cells were well dispersed in physiological saline. The dispersion was centrifuged at 4,200×g at 4° C. for 10 minutes. The supernatant was removed and the bacterial cells were recovered. The procedure of well-dispersing the recovered bacterial cells in physiological saline and subjecting the dispersion to centrifugation under the above conditions was repeated three times. The obtained bacterial cells were dispersed in ion exchanged water and heated at 80° C. for 20 minutes. The dispersion was centrifuged at 4,200×g at 4° C. for 10 minutes and the precipitate was lyophilized to give heat-killed bacterial cells (Example product 1).

Example 2

Heat-killed bacterial cells (Example product 2) were prepared in the same manner as in Example 1 except that

*Lactobacillus plantarum* JCM 1149 strain was used instead of *Lactobacillus plantarum* L-137 strain.

Preparation of Samples

Example products 1 and 2 were separately suspended in 1 mL of 50 mM sodium carbonate buffer (pH 9.6) at a concentration of 5 mg/mL. To each of the bacterial cell suspensions, fluorescein isothiocyanate (FITC) isomer-I (Dojindo Laboratories) was added at a final concentration of 5 µg/mL, and reacted at 37° C. for 60 minutes under protection from light so that the bacterial cells were labeled with FITC. The FITC-labeled bacterial cells were centrifuged at 19,000×g at 4° C. for 10 minutes. The precipitate was suspended in 1 mL of phosphate buffer and the suspension was centrifuged under the same conditions as above. After repeating three times the procedure of suspending the precipitate in phosphate buffer and subjecting the suspension to centrifugation, the residue from the centrifugation was suspended in 1 mL of phosphate buffer. The suspension was diluted 500-fold in RPMI 1640 medium containing 10% FBS.

Preparation of Phagocytes

Phagocytes were obtained from mouse spleen.

The spleen was harvested from mice (BALB/c, female, 6 to 12 weeks old) and crushed in RPMI 1640 medium containing 10% FBS. To the cell population, 0.017 M Tris buffer (pH 7.65) to which ammonium chloride had been added at a final concentration of 0.75% was added and the cells were incubated at 4° C. for 5 minutes to lyse the red blood cells. The cells were then passed through a #200 mesh to give a spleen cell suspension. The number of the cells in the spleen cell suspension was determined using an automated blood cell counter (CDA-500, Sysmex Corporation). The spleen cell suspension was suspended in RPMI 1640 medium containing 10% FBS so that the concentration of the spleen cells was $1 \times 10^7$ cells/mL. The suspension was added to a 24-well culture plate at 1 mL per well and cultured in a 5% $CO_2$ incubator at 37° C. for 90 minutes. After the culture, the liquid medium was pipetted and the liquid medium containing non-adherent cells was thoroughly removed to give an adherent cell population containing a large proportion of phagocytes. After that, 500 µL of RPMI 1640 medium containing 10% FBS was added.

Test Example 1

To 500 µL of the adherent cell population containing a large proportion of phagocytes prepared in the above Preparation of Phagocytes, each of the following was separately added in an amount of 500 µL: the FITC-labeled bacterial cells of Example products 1 and 2 prepared at a concentration of 10 µg/mL in RPMI 1640 medium containing 10% FBS (samples 1 and 2), and a control sample (sample 3) prepared with RPMI 1640 medium alone containing 10% FBS and not containing bacterial cells. Samples 1 to 3 were cultured in a 5% $CO_2$ incubator at 37° C. for 4 or 24 hours and the phagocytes were recovered. The phagocytes that took up the FITC-labeled bacterial cells among the recovered phagocytes were detected using a flow cytometer (Beckman Coulter), and the percentage of the phagocytes that took up the bacterial cells in the recovered phagocytes was calculated. The results are shown in Table 1.

TABLE 1

| | After 4 hours of culture | After 24 hours of culture |
|---|---|---|
| Sample 1 (L-137 strain) | 23% | 47% |
| Sample 2 (JCM 1149 strain) | 4% | 23% |
| Sample 3 (No bacterial cells) | 0% | 1% |

Test Example 2

To 500 µL of the adherent cell population containing a large proportion of phagocytes prepared in the above Preparation of Phagocytes was added 4 µg of a monoclonal antibody IgG2b against an A type scavenger receptor (clone RTK4530, hereinafter called an anti-scavenger A antibody) (sample 4). Separately, another sample (sample 5) was prepared in the same manner as above using 4 µg of an isotype control antibody instead of the anti-scavenger A antibody. The samples were cultured in a 5% $CO_2$ incubator at 37° C. for 1 hour. To each sample was added 500 µL of the FITC-labeled bacterial cells of Example product 1 prepared at a concentration of 10 µg/mL in RPMI 1640 medium containing 10% FBS, and the samples were cultured for 4 or 24 hours. After the culture, the phagocytes were recovered. The phagocytes that took up the FITC-labeled bacterial cells among the recovered phagocytes were detected using a flow cytometer, and the percentage of the phagocytes that took up the bacterial cells in the recovered phagocytes was calculated. The results are shown in Table 2.

TABLE 2

| | After 4 hours of culture | After 24 hours of culture |
|---|---|---|
| Sample 4 (Anti-scavenger A antibody) | 1% | 19% |
| Sample 5 (Isotype control antibody) | 24% | 45% |

The results of Test example 1 revealed that the lactic acid bacterial cells (L-137 strain and JCM 1149 strain) used in the carrier of the present invention are efficiently taken up by phagocytes.

The results of Test example 2 show that the phagocytes of which the scavenger A receptor was inactivated (the bacterial cells to which sample 4 was added) exhibited a significantly low uptake (%) of the lactic acid bacterial cells. That is, it was revealed that the uptake of the carrier of the present invention is mainly mediated by the scavenger receptor of phagocytes.

INDUSTRIAL APPLICABILITY

According to the present invention, various types of desired substances are efficiently delivered to phagocytes. The present invention provides a carrier that can be effectively used for diagnosis, prevention or treatment of a phagocyte-related disease (e.g., atherosclerosis etc.) in cases where a functional substance to be delivered is, for example, a drug for the phagocyte-related disease, and a composition comprising the carrier. Further, the present invention uses lactic acid bacteria and/or an extract thereof, which are widely used in the food and pharmaceutical fields, by taking into account that lactic acid bacteria are safe, can be mass cultured and mass produced, are relatively easy to genetically engineer, and have other advantages. Hence, according to the present invention, a highly safe carrier that effectively delivers a substance to phagocytes can be produced at low cost.

The invention claimed is:

1. A method for ameliorating atherosclerosis in a subject, comprising the first step of bringing an active ingredient selected from the group consisting of esculeogenin A, a PPAR (Peroxisome Proliferator-Activated Receptor)-γ agonist, adiponectin, and cholesterol oxidase (ChoA) into contact with *Lactobacillus plantarum* L-137 to load the *Lactobacillus plantarum* L-137 with the active ingredient, the second step of administering the product of the first step to the subject whereby the product of the first step is taken up by phagocytes, and the third step of ameliorating atherosclerosis in the subject.

2. The method according to claim 1, wherein the *Lactobacillus plantarum* L-137 strain is dead.

3. The method according to claim 1, wherein the active ingredient is taken up through a scavenger receptor of the phagocytes.

4. The method according to claim 3, wherein the scavenger receptor is a class A scavenger receptor.

5. The method according to claim 1, further comprising that the active ingredient is bound to the surface and/or inside of the *Lactobacillus plantarum* L-137 strain by chemical bonding or gene engineering.

6. The method according to claim 5, wherein the chemical bonding is selected from the group consisting of covalent bonding, polar covalent bonding, ionic bonding, electrostatic bonding, coordinate covalent bonding, aromatic binding, hydrogen bonding, dipole-dipole interaction, and van der waals interaction.

7. The method according to claim 5, wherein the gene engineering comprises expressing the active ingredient on the surface and/or inside of the *Lactobacillus plantarum* L-137 strain.

* * * * *